United States Patent [19]

Hahn et al.

[11] 4,284,836
[45] Aug. 18, 1981

[54] PROCESS FOR THE MANUFACTURE OF REACTION PRODUCTS OF CONJUGATED DIOLEFINS AND AROMATIC HYDROCARBONS

[75] Inventors: Karl Hahn; Uwe Biethan, both of Marl, Fed. Rep. of Germany

[73] Assignee: Chemische Werke Huels, A.G., Marl, Fed. Rep. of Germany

[21] Appl. No.: 91,909

[22] Filed: Nov. 6, 1979

[30] Foreign Application Priority Data

Nov. 10, 1978 [DE] Fed. Rep. of Germany ....... 2848804

[51] Int. Cl.³ .............................................. C07C 15/46
[52] U.S. Cl. .................................................. 585/438
[58] Field of Search .......................................... 585/438

[56] References Cited

FOREIGN PATENT DOCUMENTS 49-32985 3/1974 Japan .

OTHER PUBLICATIONS

Chem. Ab. 81:106301m, 1974.

*Primary Examiner*—Curtis R. Davis
*Attorney, Agent, or Firm*—Millen & White

[57] ABSTRACT

A process for preparing an alkenyl derivative of an aromatic hydrocarbon by reacting a conjugated diolefin with the aromatic hydrocarbon comprises conducting the reaction in the presence of a catalyst comprising:
1. a nickel compound which is soluble in the aromatic hydrocarbon;
2. an organo-aluminum halide; and
3. a modifying agent wherein the modifying agent (3) is a compound of the formulae

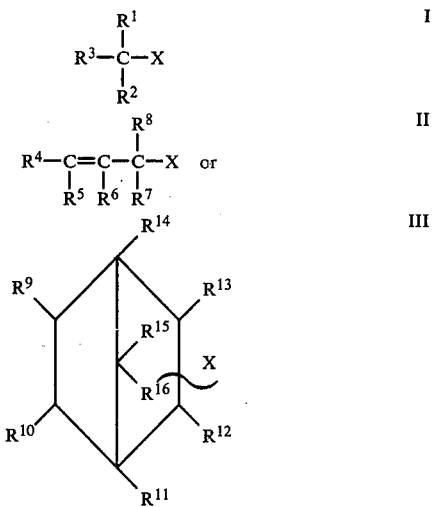

wherein
X in each case is chlorine, bromine or iodine; and
$R^1$ to $R^{16}$ independently are each a straight-chain or branched, saturated or unsaturated aliphatic or cycloaliphatic hydrocarbon radical of 1–20 carbon atoms, optionally substituted by 1–41 halogen atoms, or a hydrocarbon aryl radical of 6–14 carbon atoms, optionally substituted by
(a) 1–5 straight-chain or branched, saturated or unsaturated, aliphatic or cycloaliphatic radicals, each of 1–10 carbon atoms optionally substituted by halogen atoms, or
(b) 1–9 halogen atoms, and wherein $R^4$ to $R^{16}$ can alternatively be hydrogen, and
$R^1$ and $R^2$ can also be hydrogen when $R^3$ is optionally substituted hydrocarbon aryl as defined above, and
$R^9$ and $R^{10}$ together can alternatively form a fused-on optionally substituted ring system,
4. and, optionally, water.

9 Claims, No Drawings

PROCESS FOR THE MANUFACTURE OF REACTION PRODUCTS OF CONJUGATED DIOLEFINS AND AROMATIC HYDROCARBONS

BACKGROUND OF THE INVENTION

This invention relates to a process for reacting conjugated diolefins with aromatic hydrocarbons.

Many alkenylations of aromatic hydrocarbons by dienes have been described in the literature (for example G. A. Olah, Friedel-Crafts and Related Reactions, volume II/I). The reaction is carried out with homogeneous and heterogeneous acid catalysts and leads predominantly to alkenyl and/or dialkenyl derivatives of aromatic hydrocarbons of the general formula

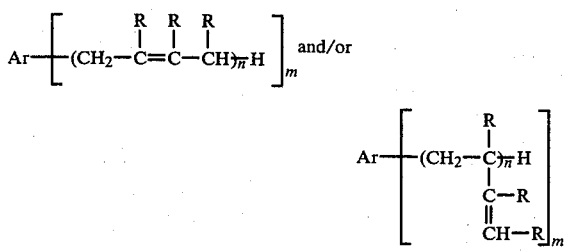

in which Ar is an aryl radical, the radicals R independently are hydrogen or alkyl radicals and n and m are each 1 or 2.

Such substances have hitherto been of only little interest. Frequently, they are only undesired by-products. Because of their high proportion of trans-double bonds, their air-drying properties are poor, and in addition they are relatively highly volatile. Longer-chain telomers (n>2) are usually formed only to a slight extent.

Such products can indeed be obtained by the processes of German Patent Specifications Nos. 1,137,727 and 1,170,932, but they also contain predominantly trans-double bonds as well as a considerable proportion of undesired highly volatile monoalkenylation products (compare also Weber et al, Brennstoff-Chemie 49, 329 et seq. (1968)). They are proposed for uses in modifications of elastomers and thermoplastics, in the field of lubricants and, after hydrogenation, in the field of detergent bases.

When Cr-III halides and alkyl-aluminum halides are used as catalysts according to the process of U.S. Pat. No. 3,373,216, products with a trans content which is relatively lower (35 to 80%) are formed; but they contain only a small proportion of incorporated aromatic radicals.

A process for the manufacture of polymers which contain aromatic hydrocarbons on a polydiene chain (the incorporation probably takes place randomly along the polydiene chain) using a nickel catalyst modified by halogen compounds of norbornene is described in Japanese Laid-Open Specification No. 49 32,985. This procedure leads to products which contain, for example, 0.5 mole of aromatic radicals per 1 mole of diene, and in some cases more than 70% of cis-1,4-double bonds. Nevertheless, this process also has a number of disadvantages. For example, the modifying agents required are not commercially available compounds and the yields are relatively low.

SUMMARY OF THE INVENTION

Accordingly, it is an object of this invention to provide a process for manufacturing reaction products of conjugated diolefins and aromatic hydrocarbons using readily accessible modifying agents whereby the reaction products, alkenyl derivatives of the aromatic hydrocarbons, are obtained in good yields, and possess a large proportion of 1,4-cis-double bonds and contain only small amounts of volatile constituents.

It is another object of this invention to provide such a process by which it is possible to adjust the content of aromatic structural units and/or the average molecular weight within wide limits.

Upon further study of the specification and appended claims, further objects and advantages of this invention will become apparent to those skilled in the art.

These objects have been achieved by this invention by providing a process in which conjugated dienes are reacted with aromatic hydrocarbons in the presence of a catalyst comprising:

1. a nickel compound which is soluble in the aromatic hydrocarbon,
2. an organo-aluminum halide,
3. a modifying agent, and optionally
4. water, wherein the modifying agent (3) is a compound of the formulae

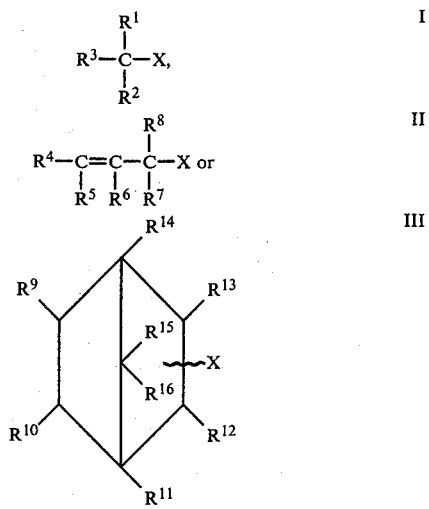

wherein
3.1 X in each case is chlorine, bromine or iodine and
3.2 $R^1$ to $R^{16}$ independently of one another
3.2.1 denote straight-chain or branched saturated or unsaturated aliphatic or cycloaliphatic hydrocarbon radicals of 1–20 carbon atoms, optionally substituted by halogen atoms, or
3.2.2 aryl radicals of 6–14 carbon atoms, optionally substituted by (a) 1–5 straight-chain or branched saturated or unsaturated aliphatic or cycloaliphatic hydrocarbon radicals, each of 1–10 carbon atoms, said radicals optionally substituted by halogen, and/or (b) halogen atoms,
3,2,3 $R^4$ to $R^{16}$ can alternatively be hydrogen, and $R^1$ and/or $R^2$ can also be hydrogen when $R^3$ is an aryl radical per 3,2,2 and
3,2,4 $R^9$ and $R^{10}$ can also be constituents of a fused-on, optionally substituted ring system.

DETAILED DISCUSSION

All conjugated dienes and aromatic hydrocarbons conventionally employed in the reaction of this invention may be used in conjunction with the inventive version thereof herein, For example, see G. A. Olah, Friedel-Crafts and Related Reactions, Volume II/1, whose disclosure is incorporated by reference herein.

Examples of conjugated dienes which can be employed in the process according to this invention are butadiene, isoprene, piperylene and 2,3-dimethylbutadiene, butadiene being preferred.

All aromatic hydrocarbons which cause no undesired side reactions, or only a slight extent of undesired side reactions, under the reaction conditions, for example benzene, toluene, xylenes, cumene or alkenyl aromatic compounds, such as styrene and butenylbenzene, can be reacted with the conjugated dienes in accordance with this invention. It is also possible, of course, to employ mixtures of such aryl compounds with each other and also mixtures which contain, in addition to the reactive aromatic hydrocarbon(s), hydrocarbons which do not react with the diene under the conditions used, such as, for example, hexane, heptane, octane and cyclohexane.

The conjugated diene is, in general, employed in a concentration of 1 to 50 percent by weight, relative to the amount of aromatic hydrocarbon employed. A concentration range of 5 to 40 percent by weight on the same basis is preferred.

The nickel compound (1) can be any nickel compound, otherwise system compatible, which is soluble in the aromatic hydrocarbon(s) used, for example nickel salts of organic carboxylic acids, preferably containing up to 20 carbon atoms, as well as complex nickel compounds, e.g., nickel octoate, nickel stearate and Ni naphthenate.

The nickel compound is, in general, employed in amounts of 0.01 to 1 mole, per 1 mole of the halogen-containing organo-aluminum compound (2). Amounts of 0.05 to 0.3 mole, per 1 mole of (2), are preferred. By "soluble" in this context, is meant sufficient solubility in the aromatic hydrocarbon(s) to permit successful operation of the process of this invention, e.g., solubilities of 0.05–5 g/ml of aromatic compound usually suffice.

Additional such nickel compounds are disclosed in U.S. Pat. No. 3,312,752 which is incorporated by reference herein.

Suitable halogen-containing organo-aluminum compounds (2) include those of the general formula $R_3Al_2X_3$, in which X is fluorine, chlorine, bromine or iodine and R is an optionally substituted aliphatic or aromatic hydrocarbon radical. R preferably represents an aliphatic hydrocarbon radical of 1 to 12 carbon atoms, in particular 1 to 4 carbon atoms. Both the three halogen radicals X and the three hydrocarbon radicals R can be identical or different. Typical and preferred representatives are $(CH_3)_3Al_2Cl_3$ and $(C_2H_5)_3Al_2Cl_3$. Substituents for R include aliphatic, cycloaliphatic and aromatic radicals with up to 14 carbon atoms.

The organo-aluminum halide is in general employed in an amount of 0.0001–0.01 mole, per mole of the conjugated diene. An amount of 0.0005–0.005 mole is preferred.

In the modifying agent (3), when any of $R^1$ to $R^{16}$ independently are aliphatic or cycloaliphatic hydrocarbon radicals, the carbon atom content in each case preferably is 1–15, especially 3–12. Such radicals include alkyl, cycloalkyl, alkenyl, cycloalkenyl, alkynyl, etc. These radicals can optionally be substituted by 1–41, e.g., 1–30 halogen atoms of F, Cl, Br and I.

When any of $R^1$ to $R^{16}$ independently are aryl radicals, such aryl radicals are hydrocarbon including phenyl, naphthyl, anthryl, phenanthryl, etc. They may be substituted by 1–5, preferably 1–3, of the aliphatic or cycloaliphatic hydrocarbon radicals of 1–10, preferably 1–8, carbon atoms which are described above. They may also be substituted by 1–9 halogen atoms (F, Cl, Br, I). The aliphatic or cycloaliphatic hydrocarbon radical substituents, in turn, may be substituted by 1–15 halogen atoms (F, Cl, Br, I).

In formula III, $R^9$ and $R^{10}$ together can also be constituents of a fused-on ring system. The fused-on ring (or ring system) may optionally be substituted.

$R^4$ to $R^{16}$ can alternatively be hydrogen, and $R^1$ and $R^2$ can also be hydrogen when $R^3$ is optionally substituted hydrocarbon aryl as defined.

Typical representatives of the modifying agents of formula I which can be employed in the process of this invention include tert-alkyl chlorides, bromides and iodides, such as, for example, tert-butyl chloride, bromide and iodide and tert-amyl chloride, bromide and iodide. Tert-butyl chloride and bromide and tert-amyl chloride are particularly suitable. Preferred representatives in the case where $R^3$ is aryl and $R^1$ and $R^2$ are hydrogen include benzyl chloride and benzyl bromide.

Examples of typical representatives of modifying agents of formula II include allyl chloride, bromide and iodide, methallyl chloride, bromide and iodide and crotyl chloride, bromide and iodide; allyl chloride, allyl bromide, methallyl chloride and crotyl chloride being particularly preferred. For the process of this invention, it is not critical whether these compounds are in the cis or trans form or in the form of an isomer mixture.

Finally, typical representatives of the modifying agents of formula III include: 2-chloro-, -bromo- and -iodo-norbornane, chloro-, bromo- and iodo-tricyclo-[5.2.1.0$^{2.6}$]-decanes and 8(9)-chloro-, -bromo- and -iodo-8,9-dihydro-tricyclo-[5.2.1.0$^{2.6}$]-dec-3-ene. 2-Chloronorbornane and 8(9)-chloro-8,9-dihydro-tricyclo-[5.2.1.0$^{2.6}$]-dec-3-ene (IV) are particularly suitable.

The modifying agents (3) are in general employed in an amount of 0.01 to 20 moles, per 1 mole of the halogen-containing organo-aluminum compound (2). An amount of 0.1–5 moles per 1 mole of (2) is preferred.

In some cases addition of a small amount of water (4) can have a favorable influence on the reaction. The water is employed in an amount of up to 1 mole, preferably in an amount of 0.05 to 0.4 mole, per 1 mole of the halogen-containing organo-aluminum compound (2).

The process of this invention is advantageously carried out in an apparatus in which a severe increase in temperature and pressure can be controlled without danger, i.e., in which addition of the diene continuously or in portions is still possible even when the pressure is increasing; an autoclave, for example, is suitable. However, the reaction can also be carried out in a batch procedure with addition of the diene in a reaction flask or in a pressure tube.

The reaction temperature can be varied within a wide range, for example from −50° to +200° C., but the temperature range from −20° to +130° C. is preferred and the range from −10° to +100° C. is particularly preferred. Reaction pressure is usually up to 30 bar. Reaction times are usually 0.1–5 hours.

The reaction products manufactured by the claimed process can be worked up and purified, for example, by first deactivating the catalyst with the necessary amount of, for example, water, alcohol or acetone and then stirring the reaction batch first with, for example, bleaching earth, and if appropriate with a basic compound, such as sodium carbonate, potassium carbonate or calcium oxide, and filtering the mixture. The amount of bleaching earth added is conventionally determined by the catalyst concentration and the size of the batch. An adequate addition can easily be established by trial experiments.

The excess solvent is then distilled off, if necessary after adding a stabilizer, such as, for example, 2,6-di-tert-butyl-p-cresol. For this working-up step, it is possible to use not only the classical conventional methods, but also, for example, distillation in a thin film evaporator. If desired, low-boiling reaction products can also be simultaneously distilled off. It is also possible, especially in the case of higher-molecular weight products, to isolate the reaction products by adding a precipitating agent which effects a phase separation. A fractionation can take place in this procedure. Examples of suitable precipitating agents are methanol, ethanol and acetone, water being added if appropriate.

Products with a broad pattern of properties, for example those with viscosities of between $\sim 50$ mPa.s and $> 10^4$ mPa.s and iodine numbers between $\sim 100$ and the range of the pure polybutadienes, can be obtained using the process of this invention. The proportion of cis-1,4-double bonds, which is favorable for many uses in practice, is on average 60-80%. The rest of the double bonds have predominantly a trans-1,4-configuration. In general, products have a number average molecular weight of 200-2000, as measured by vapor pressure osmometry.

The proportion of highly volatile products (e.g., monoalkenylation products) is quite low, e.g., 1-15 wt. % based on the weight of the final product after work-up. The aromatic content of the product is usually 0,3-3 moles of aromatic radicals per mole of diene.

Unless noted otherwise herein, all reaction conditions, procedures and details are fully conventionally determinable, e.g., in accordance with U.S. Pat. Nos. 3,312,752 and 3,329,734.

The reaction products obtained by the process of this invention are particularly suitable, if appropriate, after prior modification, such as, for example, adding on of maleic anhydride, halogenation, hydrogenation and the like, for the manufacture of air-dryable coating agents which do not pollute the environment.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following example(s), all temperatures are set forth uncorrected in degrees Celsius; unless otherwise indicated, all parts and percentages are by weight.

The characteristic values given in the examples were determined as follows:
(1) Iodine number: M. E. Tunnicliffe et al., European Polym. J. (1965) 1, 260,
(2) NMR (Microstructure and Proton Distribution): E. Pretsch et al., Tabellen zur Strukturaufklärung org. Verbindungen (Tables for Elucidating the Structure of Organic Compounds), Springer Verlag, 1976,
(3) IR: P. Simak and G. Fahrbach, Angew, Makromol, Chem. (1970) 12, 73-88, and
(4) Raman: B. Schrader, Angewandte Chemie (1973) 85, 925.

EXAMPLE 1

2 liters of toluene dried over a molecular sieve and having a temperature of 25° C. are initially introduced into a 2.5 liter glass autoclave with a double-walled jacket and a side tube. A nickel catalyst consisting of 0.6 mmol of nickel octoate (0.25 molar in toluene), 15 g of destabilized, dry butadiene and 6 mmols of ethylaluminum sesquichloride (1 molar in toluene) is then preformed. After 5 minutes, 0.4 mmol of water (as toluene saturated with water) and 8 mmols of 8(9)-chloro-8,9-dihydro-tricyclo-[5.2.1.0$^{2,6}$]-dec-3-ene (IV) (1 molar in toluene) are added and introduction of 240 g of butadiene is started immediately. (All these components, with the exception of the toluene, are added via the side tube). The rate at which the butadiene is introduced is controlled such that the temperature does not exceed 90° C. The total amount is added within a few minutes. When the addition has ended, the reaction temperature is allowed to fall to 50° C. and the solution is then kept at this temperature for an additional 1 hour. During this time, the pressure falls from a maximum value of $\sim 1.2$ bars to $\sim 0.3$ bar. The toluene solution is now drained off, deactivated with methanol, stirred with about 20 g of bleaching earth for about 1 hour and filtered. The excess toluene is then largely distilled off in vacuo.

480 g of a light yellow oil with a viscosity of 150 mPa.s and an iodine number of 155 to 159 is obtained. The content of double bonds, which is determined by IR spectroscopy, is: 21% of cis-1,4- units, 12% of trans-1,4-units and 1% of 1,2- units. A content of 19.2% of aromatic protons and 6.3% of olefinic protons is calculated from the $^1$H-NMR spectrum.

EXAMPLE 2

Example 1 is repeated with 1 liter of toluene, and the nickel catalyst is likewise preformed at 25° C. The mixture is then cooled rapidly to 0° C., the amounts of water and compound (IV) indicated in Example 1 are added and 240 g of butadiene are again admitted, and in particular such that the temperature does not exceed 75° C. The reaction batch is then kept at 50° C. for an additional 1 hour. After working-up, 275 g of an oil with a viscosity of 9,300 mPa.s is obtained. The iodine number is 247 to 253 and the content of double bonds is 34% of cis-1,4- units, 18% of trans-1,4- units and 1% of 1,2-units. The $^1$H-NMR spectrum shows a content of 10.6% of aromatic protons and 16.7% of olefinic protons.

EXAMPLES 3 to 13

The procedure was as in Example 1, but, instead of 8(9)-chloro-8,9-dihydrotricyclo-[5.2.1.0$^{2,6}$]-dec-3-ene (IV), the halogen compounds listed in the table below were employed as modifying agents in Examples 3 to 7 and 11 to 13. Using 16 mmols of alkyl chloride (Example 11), 384 g of an arylated polyoil with an iodine number of 183 to 188 and a viscosity of 360 mPa.s is obtained, and with 16 mmols of allyl bromide (Example 12), 444 g of a product with an iodine number of 110 to 115 and a viscosity of 140 mPa.s is obtained. 16 mmols of trans-crotyl chloride (Example 13) gave 486 g of a low viscosity oil (560 mPa.s) with an iodine number of 132 to 135.

TABLE

| No. | Modifying agent | (mmols) | Aromatic hydro-carbon | Reaction time (hours) | Temperature °C. Start | $T_{max}$ | Weight of Product (g) | Viscosity (mPa . s) | Iodine number |
|---|---|---|---|---|---|---|---|---|---|
| 3 | Methallyl chloride | 8 | toluene | 1 | 26 | 81 | 292 | 670 | 272 |
| 4 | Methallyl chloride | 16 | toluene | 1 | 25 | 131 | 626 | 1,300 | 58 |
| 5 | tert-butyl chloride | 16 | toluene | 1 | 35 | 99 | 341 | 910 | 198 |
| 6 | 2-Chloronor-bornane | 16 | toluene | 1 | 35 | 129 | 536 | 360 | 116 |
| 7 | Benzyl chloride | 8 | toluene | 1 | 25 | 63 | 236 | 2,000 | 325 |
| 8 | IV | 8 | m-xylene | 3 | 0 | 54 | 297 | 35,000 | 204 |
| 9 | IV | 8 | p-xylene | 2 | 0 | 52 | 281 | 32,000 | 216 |
| 10 | IV | 8 | cumene | 2 | 0 | 50 | 331 | 36,000 | 241 |

| | Microstructure (%) | | | | | | |
|---|---|---|---|---|---|---|---|
| | IR/Raman* | | | $^{13}$C-NMR | | Proton distribution (%) | |
| No. | cis-1,4 | trans-1,4 | 1,2 | cis-1,4 | trans-1,4 | olefinic H | aromatic H |
| 3 | 42 | 15 | 1 | 82 | 18 | 18.2 | 11.8 |
| 4 | ~10 | 2 | <1 | — | — | 2.7 | 24.9 |
| 5 | 25 | 13 | 1 | 84 | 16 | 11.2 | 17.5 |
| 6 | ~10 | 8 | 1 | — | — | 3.1 | 22.5 |
| 7 | 51 | 17 | 1 | — | — | 20.4 | 6.9 |
| 8 | 16 | 12 | <1 | 80 | 20 | 11.3 | 10.1 |
| 9 | 27 | 19 | <1 | 82 | 18 | 7.9 | 8.4 |
| 10 | 30 | 21 | <1 | 79 | 21 | 12.9 | 8.4 |

*absolute values

EXAMPLE 14

Instead of the Et$_3$Al$_2$Cl$_3$ used in Example 1, 6 mmols of EtAlCl$_2$ were used, but otherwise no further changes were made. With an almost unchanged reaction course ($T_{max}$: 85° C.), 409 g of a low-viscosity oil (viscosity: 30 mPa.s) with an iodine number of 148 to 149 and with 15% of cis-1,4-double bonds, 15% of trans-1,4-double bonds and 1% of vinyl double bonds (absolute values) was obtained. Accordingly, EtAlCl$_2$ as the organo-aluminum component leads to products with a lower cis-double bond content.

Et$_2$AlCl (12 mmols) instead of Et$_3$Al$_2$Cl$_3$, under the conditions described in Example 1, gave 142 g of an oil (viscosity 15,000 mPa.s) with an iodine number of 289 to 295 and with 50% of cis-1,4-double bonds, 14% of trans-1,4-double bonds and 2% of vinyl double bonds (absolute).

Accordingly, Et$_2$AlCl indeed gave the desired microstructure, but with a poorer conversion. The incorporation of aryl groups obtained is also too low for some for some fields of use.

Et$_3$Al had almost no effect under the conditions of Example 1 (weight of product: 10 g).

COMPARISON EXAMPLE A

The process was carried out as in Example 1, but 1-chloro-butane (n-butyl chloride) was employed instead of a modifying agent of formulae I to III. In a slower reaction ($T_{max}$: 53° C.), 255 g of a very highly viscous polybutadiene oil (viscosity: 110,000 mPa.s) with an iodine number of 380 to 383 and 65% of cis-1,4-double bonds, 15% of trans-1,4-double bonds and 1% of vinyl double bonds is obtained. The incorporation of aryl groups is slight. In the $^1$H-NMR spectrum, 1.3% of aromatic protons were found, in addition to 24.3% of olefinic protons.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing an alkenyl derivative of an aromatic hydrocarbon by contacting a conjugated di-olefin and the aromatic hydrocarbon with a catalyst consisting essentially of:

(a) a nickel compound which is soluble in the aromatic hydrocarbon;

(b) an organo-aluminum halide; and (c) a modifying agent wherein the modifying agent (c) is a compound of the formulae

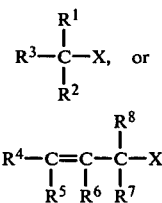

wherein

X in each case is chlorine, bromine or iodine; and

R$^1$ to R$^8$ independently are each a straight chain or branched, saturated or unsaturated, aliphatic or cycloaliphatic hydrocarbon radical of 1–20 carbon atoms, optionally substituted by 1–41 halogen atoms, or a hydrocarbon aryl radical of 6–14 carbon atoms, optionally substituted by (a) 1–5 straight-chain or branched, saturated or unsaturated, aliphatic or cycloaliphatic hydrocarbon radicals, each of 1-10 carbon atoms, optionally substituted by halogen atoms, or
(b) 1-9 halogen atoms,
and wherein, $R^4$ to $R^8$ can alternatively be hydrogen, and
$R^1$ and $R^2$ can also be hydrogen when $R^3$ is optionally substituted hydrocarbon aryl as defined above
or (c) is a chloro-, bromo- or iodo-tricyclo-[5.2.1.0$^{2.6}$]-decane or an 8(9)-chloro-, -bromo- or -iodo-8,9-dihydro-tricyclo-[5.2.1.0$^{2.6}$]-dec-3-ene.

2. The process of claim 1 wherein the catalyst further comprises:
(d) water.

3. The process of claim 1 wherein the nickel compound (a) is nickel octoate, nickel stearate or nickel naphthenate.

4. The process of claim 1 wherein the organo-aluminum halide (2) is of the formula $R_3Al_2X_3$ wherein R is an aliphatic or aromatic hydrocarbon radical of 1-12 carbon atoms and X is F, Cl, Br or I.

5. The process of claim 1 wherein the modifying agent (c) is tert-butyl chloride or bromide, tert-amyl chloride, benzyl chloride, benzyl bromide, allyl chloride or bromide methallyl chloride, crotyl chloride or 8(9)-chloro-8,9-dihydro-tricyclo-[5.2.1.0$^{2.6}$]-dec-3-ene.

6. The process of claim 1 wherein the amounts of reaction components are as follows:
conjugated diolefin: 1-50 wt % based on the amount of aromatic hydrocarbon;
nickel compound (a): 0.01-1 mole per mole of organo-aluminum halide (b);
organo-aluminum halide (b): 0.0001-0.01 mole per mole of the conjugated diolefin; and
modifying agent (c): 0.01-20 moles per 1 mole of organo-aluminum halide (b).

7. The process of claim 6 wherein water is an additional catalyst component in an amount of 0.05-0.4 mole per mole of organo-aluminum halide (b).

8. The process of claim 1 wherein the modifying agent (c) is an 8(9)-chloro-, bromo, or iodo-8,9-dihydro-tricyclo-[5.2.1.0$^{2.6}$]-dec-3-ene.

9. The process of claim 8 wherein the modifying agent is 8(9)-chloro-8,9-dihydro-tricyclo-[5.2.1.0$^{2.6}$]-dec-3-ene (IV).

* * * * *